US008580750B2

(12) United States Patent
Matuschka-Greiffenclau

(10) Patent No.: US 8,580,750 B2
(45) Date of Patent: Nov. 12, 2013

(54) COMPOSITION FOR MODERATING ALCOHOL METABOLISM AND FOR REDUCING THE RISK OF ALCOHOL INDUCED DISEASES

(75) Inventor: Markus Graf Von Matuschka-Greiffenclau, Bischofszell (CH)

(73) Assignee: TIMA Foundation, Balzers (LI)

( * ) Notice: Subject to any disclaimer, the term of this patent is extended or adjusted under 35 U.S.C. 154(b) by 839 days.

(21) Appl. No.: 11/997,127

(22) PCT Filed: Jul. 27, 2006

(86) PCT No.: PCT/EP2006/007466
§ 371 (c)(1),
(2), (4) Date: Aug. 21, 2008

(87) PCT Pub. No.: WO2007/017139
PCT Pub. Date: Feb. 15, 2007

(65) Prior Publication Data
US 2009/0054351 A1 Feb. 26, 2009

(30) Foreign Application Priority Data

| Jul. 29, 2005 | (EP) | 05016563 |
| Jul. 29, 2005 | (EP) | 05016564 |
| Jul. 29, 2005 | (EP) | 05016565 |
| Jul. 29, 2005 | (EP) | 05016566 |
| Jul. 29, 2005 | (EP) | 05016567 |
| Jul. 29, 2005 | (EP) | 05016568 |
| Aug. 24, 2005 | (WO) | PCT/EP2005/009147 |
| Aug. 24, 2005 | (WO) | PCT/EP2005/009148 |
| Aug. 24, 2005 | (WO) | PCT/EP2005/009149 |
| Aug. 24, 2005 | (WO) | PCT/EP2005/009150 |
| Aug. 24, 2005 | (WO) | PCT/EP2005/009151 |
| Aug. 24, 2005 | (WO) | PCT/EP2005/009152 |
| Aug. 24, 2005 | (WO) | PCT/EP2005/009153 |

(51) Int. Cl.
*A61K 31/7004* (2006.01)

(52) U.S. Cl.
USPC ............................................................ 514/23

(58) Field of Classification Search
USPC ............................................................ 514/23
See application file for complete search history.

(56) References Cited

U.S. PATENT DOCUMENTS

| 4,496,548 | A | 1/1985 | Moldowan et al. | |
| 5,475,031 | A | 12/1995 | Livingston | |
| 5,559,152 | A | 9/1996 | Komissarova et al. | |
| 5,989,583 | A | 11/1999 | Amselem | |
| 6,299,896 | B1 * | 10/2001 | Cooper et al. | 424/441 |
| 6,630,158 | B2 | 10/2003 | Popp et al. | |
| 2001/0033881 | A1 | 10/2001 | Fuchs et al. | 426/72 |
| 2002/0006910 | A1 | 1/2002 | Miasnikov et al. | 514/23 |
| 2002/0182196 | A1 | 12/2002 | McCleary | |
| 2003/0124198 | A1 | 7/2003 | Crum | |
| 2003/0176365 | A1 * | 9/2003 | Blass | 514/23 |
| 2005/0019427 | A1 | 1/2005 | Langeland | |
| 2005/0238710 | A1 * | 10/2005 | Connolly | 424/464 |

FOREIGN PATENT DOCUMENTS

| CN | 1058914 | 2/1992 |
| CN | 1170578 | 1/1998 |
| DE | 10326822 | 1/2005 |
| EP | 0 185 117 | 6/1986 |
| EP | 0 234 464 | 9/1987 |
| EP | 0652012 | 5/1995 |
| EP | 1195159 | 4/2002 |
| EP | 1415657 | 5/2004 |
| EP | 1304046 | 5/2006 |
| FR | 2748935 | 5/1996 |
| GB | 2029220 | 3/1980 |
| GB | 2 118 437 | 11/1983 |
| GB | 2308810 | 7/1997 |
| JP | S62-277325 | 12/1987 |
| JP | 02124084 | 5/1990 |
| JP | H3-52810 | 3/1991 |
| JP | H4-342528 | 11/1992 |
| JP | H6-510547 | 11/1994 |
| JP | H7-33653 | 2/1995 |
| JP | 2003-137788 | 5/2003 |
| RU | 2012350 | 5/1994 |
| RU | 2240789 | 11/2004 |
| WO | WO 98/41113 | 9/1998 |
| WO | WO 01/67890 | 9/2001 |
| WO | WO 01/85178 | 11/2001 |

(Continued)

OTHER PUBLICATIONS

Edited by Bennett, C. J. and Plum, F. Cecil Textbook of Medicine, 20th Edition, vol. 2; Damasio, Antonio R. "Alzheimer's Disease and Related Dementias", pp. 1892-1896. (1996).*

(Continued)

*Primary Examiner* — Wu-Cheng Winston Shen
*Assistant Examiner* — Yih-Horing Shiao
(74) *Attorney, Agent, or Firm* — Parker Highlander PLLC

(57) ABSTRACT

The present invention is directed to a composition of matter, in particular a food composition, dietary or food supplementation, and pharmaceutical composition, respectively. The composition of matter reduces the risk of neuropathy, neurodegenerative diseases including late-onset Alzheimer's disease, and cancer, in particular of pancreatic, esophageal, oropharyngolaryngeal, liver, colorectal, lung and/or breast cancer, in particular the drug and/or alcohol induced risk of said diseases. In this respect, the present invention is also directed to a composition of matter; in particular a food composition, dietary or food supplementation, and pharmaceutical composition, respectively, which supports and/or moderates the alcohol degradation process within the human body.

4 Claims, 4 Drawing Sheets

(56) References Cited

FOREIGN PATENT DOCUMENTS

| WO | WO 03/006073 | 1/2003 |
|---|---|---|
| WO | WO 04/032916 | 4/2004 |
| WO | WO 04/037015 | 5/2004 |
| WO | WO 04/037018 | 5/2004 |
| WO | WO 2005/077464 | 8/2005 |

OTHER PUBLICATIONS

MayoClinic.com "Migraine"; also available at http://www.mayoclinic.com/health/migraine-headache/DS00120/Dsection=treatments-and-drugs; last viewed Oct. 20, 2010.*

Zips, D. et al., In vivo, "New Anticancer Agents: In Vitro and In Vivo Evaluation", vol. 19, pp. 1-8 (2005).*

Kim, J.-M. et al., Neurobiology of Aging, "Assessment of association between mitochondrial aldehyde dehydrogenase polymorphism and Alzheimer's disease in an older Korean population", vol. 25, pp. 295-301 (2004).*

Purohit, V. et al., Alcohol, "Mechanisms of alcohol-associated cancers: introduction and summary of the symposium", vol. 35, pp. 155-160 (2005).*

Blot et al., "Nutrition Intervention Trials in Linxian, China: Supplementation With Specific Vitamin/Mineral Combinations, Cancer Incidence, and Disease-Specific Mortality in the General Population," *J. Nat. Cancer Inst.*, 85(18):1483-1491, 1993.

Boffetta and Hashibe, "Alcohol and cancer," *Lancet Oncology*, 7:149-156, 2006.

Database WPI, Section Ch, Week 199252, Derwent Publications Ltd., Database Accession Number: AN 1992-424810, dated Feb. 26, 1992 (Corresponding to CN1058914).

Database WPI, Section Ch, Week 199505, Derwent Publications Ltd., Database Accession Number: AN 1995-034579, dated May 15, 1994 (Corresponding to RU2012350).

Database WPI, Section Ch, Week 200326, Derwent Publications Ltd., Database Accession Number: AN 2003-257485, dated Jan. 21, 1998 (Corresponding to CN1170578).

Database WPI, Section Ch, Week 200506, Derwent Publications Ltd., Database Accession Number: AN 2005-055600, dated Nov. 27, 2004 (Corresponding to RU2240789).

Dawsey et al., "Effects of vitamin/mineral supplementation on the prevalence of histological dysplasia and early cancer of the esophagus and stomach: results from the Dysplasia Trial in Linxian, China," *Cancer Epidemiology*, 3(2):167-172, 1994.

Kalapothaki et al., "Nutrient intake and cancer of the pancreas: a case-control study in Athens, Greece," *Cancer Causes and Control*, 4(4):383-389, 1993.

Lesperance et al., "Mega-does vitamins and minerals in the treatment of non-metastatic breast cancer: an historical cohort study," *Breast Cancer Res. and Treatment*, 76(2):137-143, 2002.

Olsen et al., "Nutrients and pancreatic cancer: a population-based case-control study," *Cancer Causes and Control*, 2(5):291-297, 1991.

PCT International Report on Patentability, issued in International Application No. PCT/EP2006/007466, dated Jan. 29, 2008.

PCT International Search Report, issued in International Application No. PCT/EP2006/007466, dated Nov. 24, 2006.

PCT Written Opinion of the International Searching Authority, issued in International Application No. PCT/EP2006/007466, dated Jan. 29, 2008.

Zhang et al., "Dietary Carotenoids and Vitamins A, C, and E and Risk of Breast Cancer," *J. Nat. Cancer Inst.*, 91(6):547-548, 1999.

Freudenheim et al., "Alcohol consumption and risk of lung cancer: a pooled analysis of cohort studies," *Am. J. Clin. Nutr.*, 82:657-67, 2005.

Le Marchand et al., "Associations of sedentary lifestyle, obesity, smoking, alcohol use, and diabetes with the risk of colorectal cancer," *Cancer Research*, 57:4787-4794, 1997.

Office Communication, issued in Chinese Patent Application No. 200680027840.0, dated Jan. 5, 2011.

"Clinic analysis of 72 examples of alcoholic cirrhosis," *Shan Xi Clinical Medicine*, 10(8):594, 2001. (English translation).

"Clinic study of the treatment of liver-protecting, antialcoholismic troche for alcoholic liver disease," *Drug Research*, 10(4):8, 2001. (English translation of Chinese publication).

"Diagnosis and treatment of alcoholic liver disease," *Chinese Journal of Hepatology*, 9(5):313, 2001.

"Treatment of acute alcoholism and complicated multiple organ failure with the combination of traditional Chinese medicine and Western medicine," *Journal of Emergency in Traditional Chinese Medicine*, 11(1):69, 2002. (English translation of Chinese publication).

"Twenty methods for relieving alcoholism," *Safety and Health*, Issue 3, p. 53, 2001. (English translation of Chinese publication).

Hobara et al., "Effect of quinine derivatives on ethanol and acetaldehyde metabolism in rats," *Japanese Society of Pharmaceutical Health Care and Sciences*, 15(1):33-35, 1989. (English abstract of Japanese publication).

Mansouri et al., "Acute ethanol administration oxidatively damages and depletes mitochondrial DNA in mouse liver, brain, heart, and skeletal muscles: protective effects of antioxidants," *The Journal of Pharmacology and Experimental Therapeutics*, 298(2):737-743, 2001.

Office Action issued in Chinese Application No. 200580005272 (English translation thereof), dated May 7, 2010.

Office Action issued in Japanese Application No. 2006-553537 (English translation thereof), dated Jun. 8, 2011.

Office Action issued in Japanese Application No. 2011-266675 (English translation thereof), dated Feb. 6, 2012.

Office Action issued in U.S. Appl. No. 10/589,674, mailed Apr. 11, 2013.

Office Action issued in U.S. Appl. No. 10/589,674, mailed Aug. 12, 2011.

Office Action issued in U.S. Appl. No. 10/589,674, mailed Mar. 10, 2010.

Office Action issued in U.S. Appl. No. 10/589,674, mailed Mar. 29, 2012.

Office Action issued in U.S. Appl. No. 10/589,674, mailed Oct. 5, 2009.

Office Action issued in U.S. Appl. No. 10/589,674, mailed Oct. 27, 2010.

* cited by examiner

COMPOSITION FOR MODERATING ALCOHOL METABOLISM AND FOR REDUCING THE RISK OF ALCOHOL INDUCED DISEASES

This application is a national phase application under 35 U.S.C. §371 of International Application No. PCT/EP2006/007466 filed Jul. 27, 2006, which claims priority to European Patent Application No. 05016568.7 filed Jul. 29, 2005, European Patent Application No. 05016567.9 filed Jul. 29, 2005, European Patent Application No. 05016566.1 filed Jul. 29, 2005, European Patent Application No. 05016565.3 filed Jul. 29, 2005, European Patent Application No. 05016563.8 filed Jul. 29, 2005, European Patent Application No. 05016564.6 filed Jul. 29, 2005, International Application No. PCT/EP2005/009148 filed Aug. 24, 2005, International Application No. PCT/EP2005/009147 filed Aug. 24, 2005, International Application No. PCT/EP2005/009150 filed Aug. 24, 2005, International Application No. PCT/EP2005/009151 filed Aug. 24, 2005, International Application No. PCT/EP2005/009149 filed Aug. 24, 2005, International Application No. PCT/EP2005/009152 filed Aug. 24, 2005, International Application No. PCT/EP2005/009153 filed Aug. 24, 2005. The entire text of each of the above-referenced disclosures is specifically incorporated herein by reference without disclaimer.

The present invention is directed to a composition of matter, in particular a food composition, dietary or food supplementation, and pharmaceutical composition, respectively. The composition of matter reduces the risk of neuropathy, neurodegenerative diseases including late-onset Alzheimer's disease, and cancer, in particular of pancreatic, esophageal, oropharyngolaryngeal, liver, colorectal, lung and/or breast cancer, in particular the drug and/or alcohol induced risk of said diseases. In this respect, the present invention is also directed to a composition of matter, in particular a food composition, dietary or food supplementation, and pharmaceutical composition, respectively, which supports and/or moderates the alcohol degradation process within the human body.

The present invention particularly addresses the problem of accumulation of acetaldehyde after rapid alcohol degradation i.e. alcohol metabolism as may occur in most people of Non-Caucasian type genetic structure.

It is assumed that drinking alcoholic beverages is associated with an increased risk for neuropathy diseases. Ethanol induces a lot of effects on the brain and nerve system which leads to change in behaviour, motor coordination and, in the extreme case, brain damage. In particular, peripheral nerve polyneuropathy is commonly observed in alcoholic patients. One possible mediator of the alcohol effects is acetaldehyde, a highly toxic metabolite of ethanol. Acetaldehyde is a highly reactive molecule with oxidative activity and has cytotoxic effects and modifies proteins in the cells, leading to their dysfunction.

It is also assumed that drinking alcoholic beverages is associated with an increased risk for neurodegenerative diseases. These diseases are expected as being caused by the deposition of inclusion bodies in the neuronal cells, and finally disappearance of the cells. Oxidative stress and the following lipid peroxidation caused by oxidants, such as reactive oxygen species, are reported to play an important role in the pathogenesis of neurodegenerative diseases including Alzheimer's disease, Parkinson's disease, and cerebral ischemia. Acetaldehyde is thus thought to be the cause of several alcohol-induced neuronal changes. Acetaldehyde is also suspected to play a pivotal role in the development of alcohol related cancers because of its established DNA damaging effects (single-strand and double-strand breaks) and carcinogenicity in laboratory animals.

It is also assumed that drinking alcoholic beverages is associated with an increased risk for certain kinds of cancer including pancreatic, liver, colorectal, lung, breast, esophageal and oropharyngolarynal cancer. The association of alcohol consumption with increased risk for esophageal and oropharyngolarynal cancer is considered as being evident at least implicitly from epidemiological studies indicating that alcohol itself and/or its metabolite(s) has carcinogenic potency.

Furthermore, increased estrogen levels in women drinkers appear to be an important mechanism for development of breast cancer. One possible mechanism for the increase of estrogen is that overproduced acetic acid after drinking is converted to steroids. The possible role of acetaldehyde for the alcohol-induced breast cancer appears to be evident.

A very recent paper (Lancet Oncol 7: 149-156, 2006) discussed the relationship between alcohol consumption and the risk of colorectal cancer and lung cancer.

Ethanol taken into the body is eliminated by its oxidation, mainly in the liver. Ethanol ($CH_3CH_2OH$) is first metabolised to acetaldehyde ($CH_3CHO$) by alcohol dehydrogenase (ADH), and then acetaldehyde ($CH_3CHO$) is further metabolised to acetic acid ($CH_3COOH$) by aldehyde dehydrogenase (ALDH), mainly by liver aldehyde dehydrogenase 2 (ALDH2).

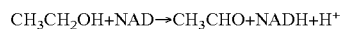

$$CH_3CH_2OH+NAD \rightarrow CH_3CHO+NADH+H^+$$

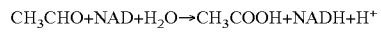

$$CH_3CHO+NAD+H_2O \rightarrow CH_3COOH+NADH+H^+$$

Most of acetaldehyde generated during alcohol metabolism is promptly eliminated by ALDH2, the low Km ALDH. There are polymorphic isoforms of ALDH and class 2 ALDH (ALDH2), which has the lowest affinity constant (Km), is the most important enzyme for acetaldehyde oxidation. A mutant allele, ALDH2*2, has a single point mutation (GSA) in exon 12 of the active ALDH2*1 gene. This mutation results in a substitution of glutamic acid (Glu) at amino acid position 487 by lysine (Lys). ALDH2*2 encodes thus a catalytically inactive subunit and acts in a dominant negative fashion. Individuals with heterozygous ALDH2*1/2*2 genotype should have only 6% activity compared to those with normal homozygous ALDH2*1/2*1 genotype. Distribution of ALDH2*2 allele varies by race: it is prevalent in East Asia but has not been found in Caucasians and Africans, who have the active ALDH2*1 allele. 40-50% of East Asians have the inactive ALDH2*2 allele. The average peaks of blood acetaldehyde concentrations of ALDH2*1/2*2 heterozygotes and ALDH2*2/2*2 homozygotes after drinking of a small amount of ethanol (0.1 g/kg body weight) are five times and 18 times, respectively, of that found in ALDH2*1/2*1 homozygotes after drinking of moderate amount of ethanol (0.8 g/kg body weight). The amount of acetaldehyde in saliva is increased in ALDH2*1/2*2 heterozygotes given alcohol, and its level falls when alcohol oxidation of active ALDH2*1/2*1 homozygotes is inhibited by an ALDH inhibitor 4-methylpyrazol. Therefore, acetaldehyde oxidation is strikingly impaired in individuals with ALDH2*2 allele.

Deficiency of ALDH2 activity is associated with increased the risk of cancer and therefore acetaldehyde is regarded as a carcinogen. In fact, acetaldehyde can damage culture hepatocytes and results in secondary hyperproliferation.

It appears also evident that ALDH2 deficiency is associated with an increased risk of polyneuropathy and of late-onset Alzheimer's disease. Moreover, sensory conduction time is significantly longer in Japanese alcoholic patients with hypoactive ALDH2*2 allele than that in active ALDH2*1/2*1 homozygotes, indicating dysfunction of peripheral neurons of the formers. The experimental neuronal cell system, in which ALDH is genetically inactivated, becomes highly vulnerable to exogenously added aldehyde metabolite, indicating that oxidative stress caused by acetaldehyde considerably damage neuronal cells. These results collectively suggest that oxidative stress induced by acetaldehyde may damage mitochondrial energy production and modify proteins in the neuronal cells, leading to form the deposition of modified proteins. These changes further damage cellular function and finally cause cell death. Therefore, acetaldehyde may closely be involved in the pathogenesis of polyneuropathy and/or neurodegenerative diseases such as late-onset Alzheimer's disease.

It is also assumed that ALDH2 deficiency is associated with an increase of the risk of breast cancer. Acetaldehyde has a lipophilic nature and accumulates in adipose tissues. Mammary gland is enriched in fat and other lipophilic tissues. It is concluded that drinking alcoholic beverages is associated with increases risk for breast cancer. The possible role of acetaldehyde for the alcohol-induced breast cancer is thus assumed as well.

For liver cancer it is known that Hepatitis viruses (HV), especially HVB and HVC, increase the risk of liver cancer. However, epidemiological surveys are considered to support that ALDH2 deficiency is also associated with an increased risk of liver cancer for alcohol drinkers with or without hepatitis viruses. This supports the notion that acetaldehyde is closely involved in the carcinogenesis of hepatocytes in human alcohol drinkers.

Additionally, it appears to be evident that alcoholic beverages are carcinogenic to humans and causally related to cancer of the oral cavity, pharynx, larynx and esophagus. In particular, it appears that ALDH2 deficiency is also associated with increased the risk of cancer of the oral cavity, pharynx, larynx and esophagus. Epithelial cells in these upper digestive tract are attacked by acetaldehyde not only diffused from blood but also secreted from salivary glands after drinking, especially in persons with ALDH2*2 allele. The supplement mix according to the invention accelerates the disappearance of alcohol and acetaldehyde after drinking in not only ALDH2*1/2*1 homozygotes but ALDH2*1/2*2 heterozygotes. The supplement according to the invention effectively accelerates alcohol metabolism, and is expected to suppress the secretion of acetaldehyde from salivary glands. Therefore, the supplement according to the invention can be used to diminish the risk of cancer of the oral cavity, pharynx, larynx and esophagus.

In Japan, alcoholic pancreatitis is the most common type (68.5%) of chronic pancreatitis in males. Chronic pancreatitis has been indicated as a risk factor for pancreatic cancer. While Smoking is a well-documented risk factor for the development of pancreatic cancer, it appears that ALDH2 deficiency increases the risk of pancreatic cancer in smokers and it is assumed that alcohol increases the risk of pancreatic cancer of smokers. These data collectively suggest that alcohol, most possibly its metabolite acetaldehyde, takes part in the carcinogenesis of pancreatic cells.

It appears that ALDH2 deficiency is also associated with an increase of the risk of pancreatic cancer. Epithelial cells in these upper digestive tract are attacked by acetaldehyde not only diffused from blood but also secreted from salivary glands after drinking especially in persons with ALDH2*7 allele.

Therefore, it is an object of the present invention to provide compositions effective in reducing alcohol induced diseases.

The object is solved by the subject-matter as defined in the claims.

The following figure is part of the present description and is included to demonstrate a certain aspect of the present invention. The invention may be better understood by reference to this figure in combination with the detailed description of specific embodiments presented herein.

FIG. 1 shows in a diagram the effects of the composition according to the present invention on alcohol enhanced metastasis of RPMI4788. ETOH means ethanol; SUP means composition according to the present invention; 4788 means RPMI4788 cells.

Figure 1:
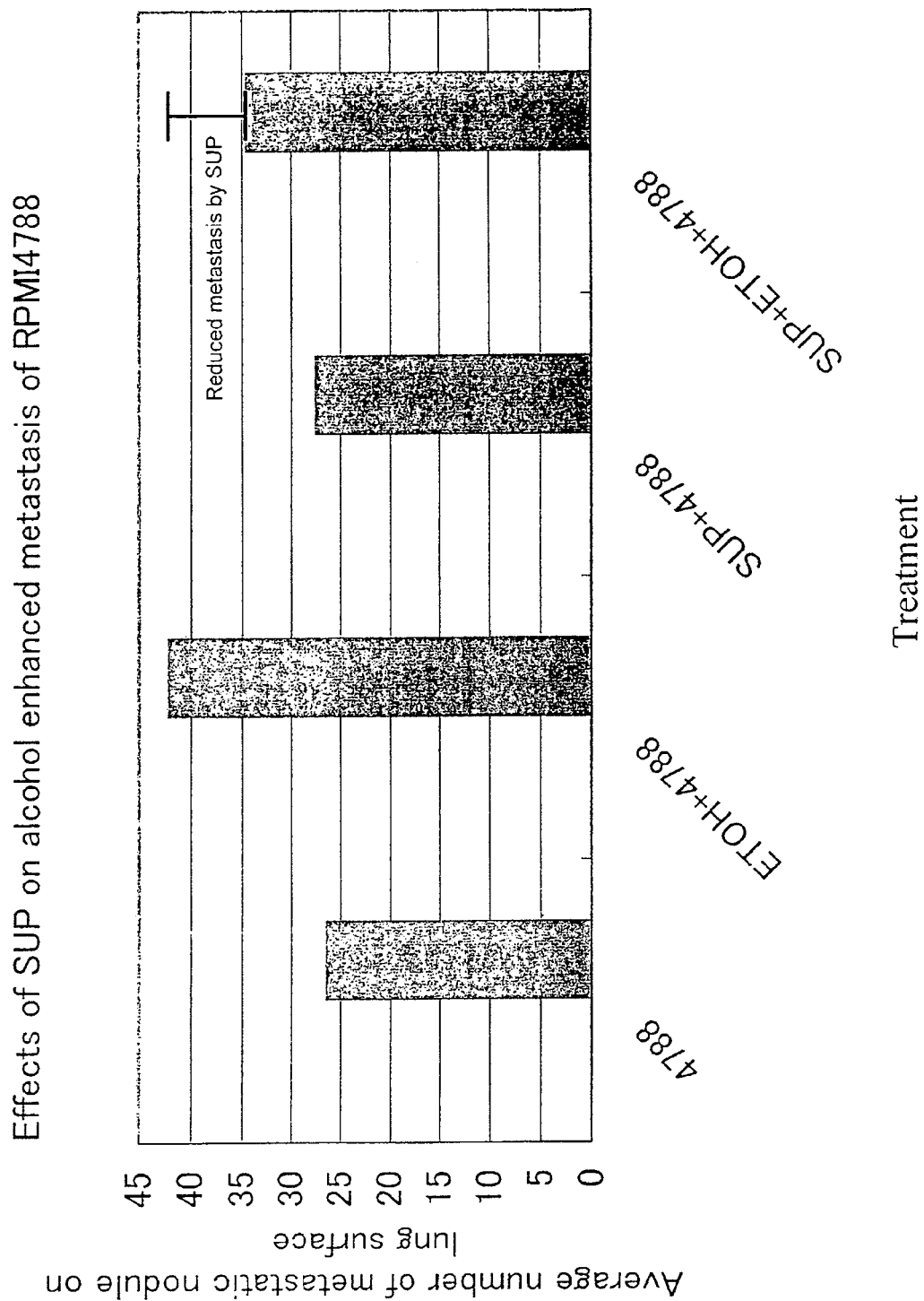
Figure 2:
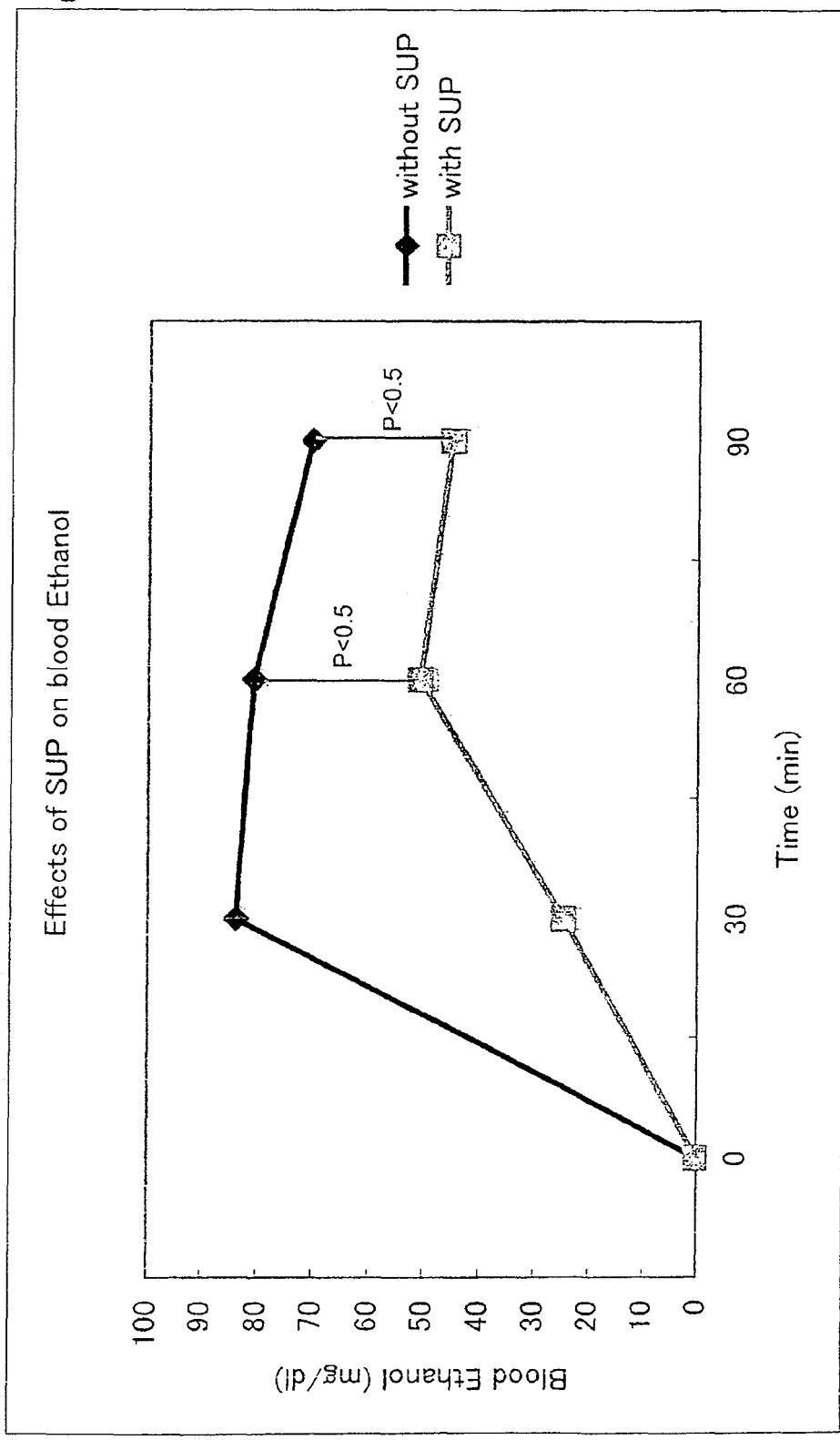
FIG. 2 shows in a diagram the effect of the composition according to the present invention on the blood ethanol level. SUP means composition according to the present invention.
Figure 3:
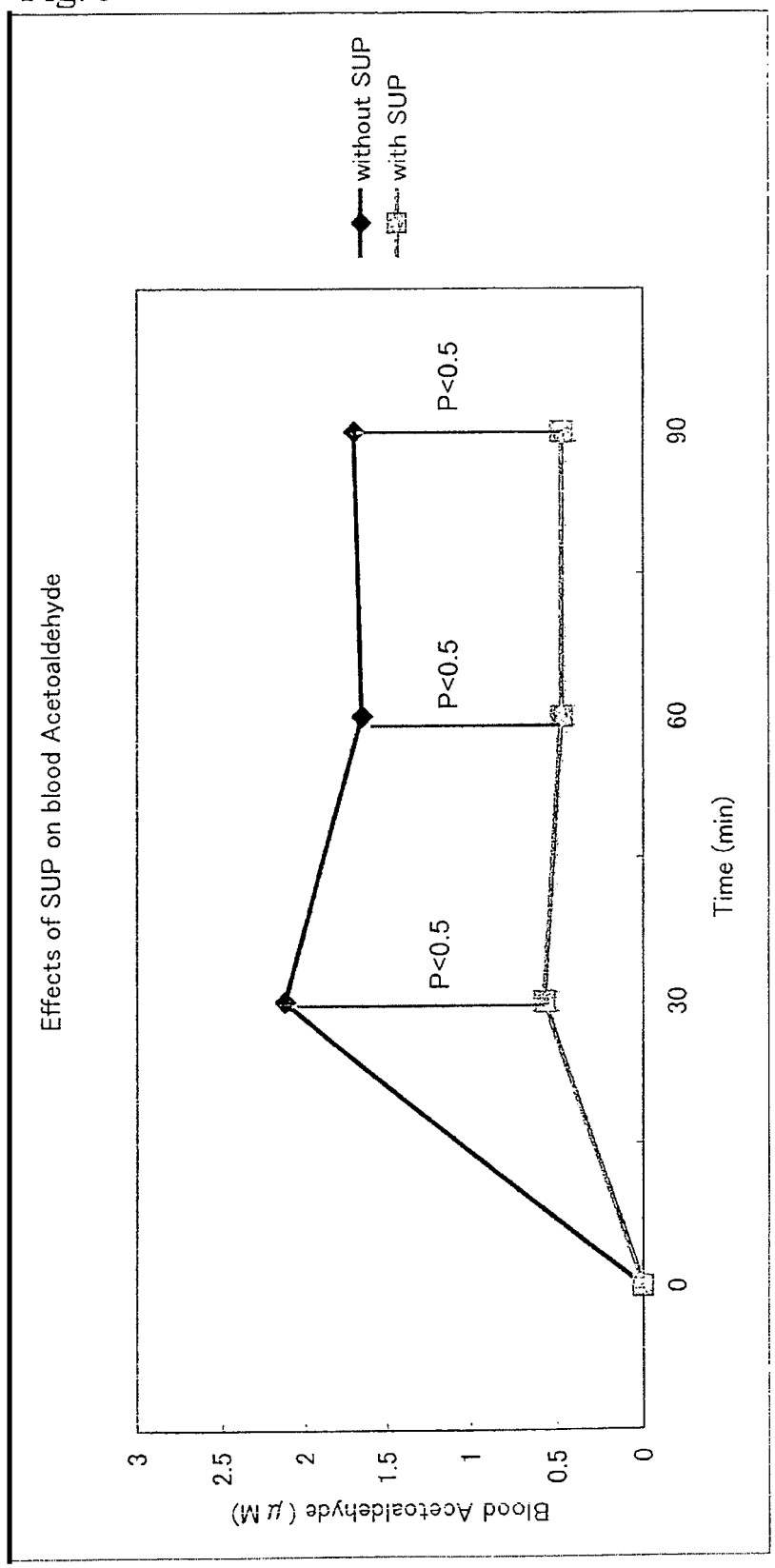
FIG. 3 shows in a diagram the effect of the composition according to the present invention on the acetaldehyde level. SUP means composition according to the present invention.
Figure 4:
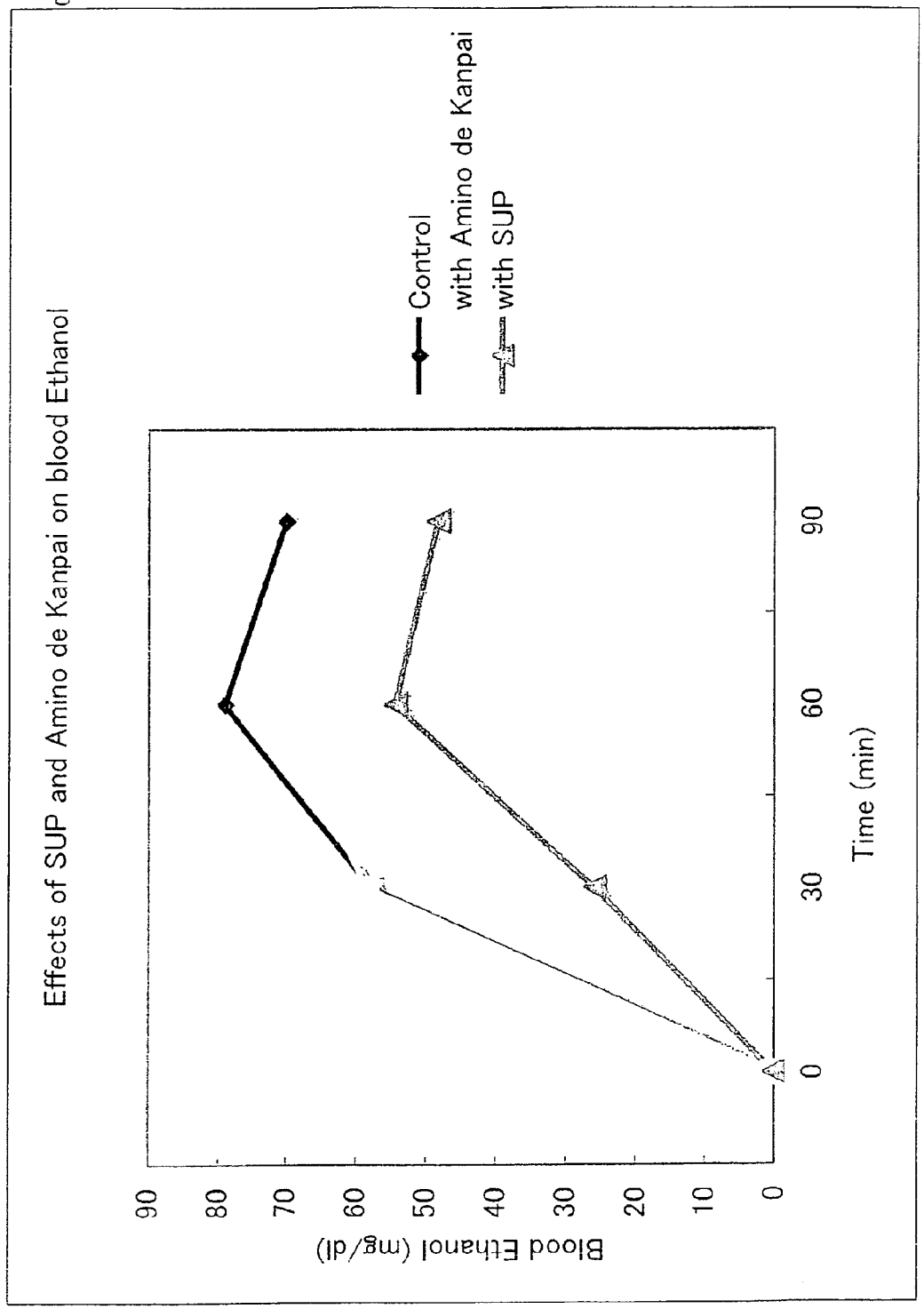
FIG. 4 shows in a diagram the effect of the composition according to the present invention in comparison to Amino de Kanpai on the blood ethanol level. SUP means composition according to the present invention.

The term "neuropathy" as used herein, refers to any disease or abnormality of the neurons of the nervous system. "In particular "neuropathy" means a disorder of the peripheral nervous system, affecting nerves anywhere except brain and the spinal cord. A non-limiting example for neuropathy is alcoholic polyneuropahy which is characterized by numbness, abnormal sensations called dysesthesias and allodynias that occur either spontaneously or in reaction to external stimuli, and a characteristic form of pain, called neuropathic pain or neuralgia.

The term "neurodegenerative disease" as used herein, refers to any disease or abnormality of the of the nervous system caused by deterioration of neurons, which include death of neurons and functional loss of neurotransmitters. Non-limiting examples for a neurodegenerative disease are Alzheimer's disease and Parkinson's disease.

The term "food composition" as used herein, refers to any kind of composition which is eatable and/or drinkable without causing toxic symptoms in the subject eating or drinking the respective composition.

The term "supplement", "dietary supplement" or "food supplement" as used herein, refers to a composition which is consumed in addition to the daily meals or in between.

The term "late-onset Alzheimer's Disease" as used herein, refers to the onset of Alzheimer's Disease in elderly people, in particular in people being 65 years old and older.

The term "flushing syndrome" as used herein, refers to the flushing as a consequence of drinking alcohol. Flushing is associated with the erythema (reddening caused by dilation of capillaries) of the face, neck, and shoulder, after consumption of alcohol. Flushing after alcohol consumption is often associated with a range of symptoms: dizziness, nausea, headaches, an increased pulse, occasional extreme drowsiness, and occasional skin swelling and itchiness. There symptoms are collectively called "Flushing syndrome" or "Asian flush".

The term "oropharyngolaryngeal cancer" as used herein, refers to cancers derived from oral cavity, pharynx, larynx or upper esophagus. At early stage of the cancer of this area, the origin could be determined. However, very often, the cancer of this area is found at the late invasive stage and the origin cannot be determined. Therefore, cancers arising from this sources are collectively termed "oropharyngolaryngeal cancer".

The term "dosage form" as used herein, refers to an amount of medication to be taken at one time, optionally in regular intervals.

According to the present invention the object is attained by a composition of matter comprising the following substances:

dextrose, Vitamin C, L-glutamine and/or L-glutamic acid, cysteine, riboflavin, succinic acid, fumaric acid, coenzyme Q10, and niacin.

The composition according to the present invention reduces the activity or suppresses the production of a particular alcohol dehydrogenase enzyme, namely the $ADH_3$, so that the production of acetaldehyde and the ethanol metabolism process is slowed down and the alcohol induced peak load on the human organism is reduced. Furthermore, the enzymatic activity of the aldehyde dehydrogenase $ALDH_2$ is enhanced, so that the metabolisation of acetaldehyde is supported.

The composition of matter according to the present invention accelerates the disappearance of alcohol and acetaldehyde after drinking. The composition is active preferably in ALDH2*1/2*1 homozygote and ALDH2*1/2*2 heterozygote subjects. The composition according to the present invention effectively accelerates alcohol metabolism and suppresses the secretion of acetaldehyde from salivary glands. Therefore, the composition according to the present invention can be used to diminish the risk of neuropathy, neurodegenerative diseases, e.g. late-onset Alzheimer's disease, and of cancer, in particular of pancreatic, esophageal, oropharyngolarynal, colorectal, lung, liver and breast cancer.

By reducing the peak of excess acetaldehyde entering the blood stream, thereby lowering the risk of damage to vital organs and functions of the human body, the composition according to the present invention lowers the risk of several forms of cancer such as pancreatic, esophageal, oropharyngolarynal, colorectal, lung, liver and/or breast cancer.

By decreasing the concentration of blood acetaldehyde after drinking the composition according to the present invention decreases the risk of pancreatic cancer, preferably for alcohol drinkers with smoking habit, especially those who have the ALDH2*2 allele.

By eliminating acetic acid through activation of the tricarboxylic acid (TCA) cycle and electron transport system, and consequently by preventing the synthesis of steroids including estrogen the composition according to the invention reduces the risk of breast and liver cancer, preferably for alcohol drinkers, especially those who have the ALDH2*2 allele.

The composition of matter according to the present invention contains several substances, which are often deficient in patients with alcoholic neuropathy. The composition is thus effective in reducing a flushing syndrome, reducing the likelihood of headaches and also helps to avoid or ease an alcohol induced hangover the day after. The niacin-fraction (Vitamin B3) included in the composition functions as nicotinamide adenine dinucleotide (AD), which is effective towards a coenzyme to alcohol dehydrogenase (ADH) and aldehyde dehydrogenase (ALDH). This vitamin is provided to accelerate ethanol metabolism.

According to a particularly preferred embodiment, the composition also includes pantotheic acid, in particular in the range of about 1 to about 5 mg. Pantotheic acid functions as coenzyme A (CoA), which is considered necessary to metabolize acetic acid. Acetic acid is activated in conjugation with CoA to form acetyl-CoA, which is metabolized in TCA cycle. In enzymatical point of view, elimination of a product (acetic acid) is effective towards an acceleration of the metabolism of a substrate (acetaldehyde).

Preferably this composition should be taken about 5 minutes prior to consumption of alcohol and in case of high alcohol consumption again whilst consuming alcohol. The mass of the composition taken by the consumer should be in the range of about 70 to 120% of the mass of the alcohol included in the consumed drinks. A standard dose might include about 10.0 g dextrose, 1.0 cg Vitamin C, 1.5 g L-glutamine and/or L-Glutamic acid, 500 mg cysteine, 40 mg riboflavin, 100 mg succinic acid, 100 mg fumaric acid, 60 mg coenzyme Q10, and about 10 mg Niacin (Vitamin B3). Preferably the relation of the components of the composition is oriented towards the above given relation. The overall dosage may be adapted to the body mass weight of the consumer.

The composition according to the present invention is intended to prevent too much acetaldehyde passing into the mitochondrial matrix and to suppress self blockade of the enzymatic activity of ALDH and thus facilitate the decomposition of acetaldehyde.

The physiological risks in connection with alcohol consumption may therefore be significantly reduced by the use of the composition according to the present invention, as this composition facilitates in a synergetic manner an early decrease of the level of acetaldehyde after drinking and simultaneously provides a protective effect in respect of the suppression of the generation of free radicals.

If the composition is to be administered as a food composition or dietary supplementation it is preferably in such a form, preferably as ingredients of a kind of aperitif, that it allows the food composition to be consumed within a restaurant or a bar prior to consuming alcoholic drinks. The food composition or dietary supplementation is preferably constituted in a manner Wherein a dosage of same is in the form of tablets. Preferably, each tablet is so shaped and dimensioned that it allows said tablet to be easily swallowed. Preferably, said tablets are in such a form that one dosage includes a plurality of those tablets. The tablets may be accommodated within a dosage receptacle which includes a number of those tablets. It is possible for the food composition to be in the form of small tablets or balls, and to keep same in a small tube, while the volume of the food composition taken by the consumer can be determined with respect to the volume of alcohol which is expected to be consumed. The composition or dietary supplementation may also be in a form similar to sugar-cubes, or might be in the form of cryopowder. The composition or dietary supplementation may be separated into separate subunits. It is possible to provide one unit, for example a capsule including the Vitamin C fraction, cysteine, riboflavin, succinic acid, fumaric acid and coenzyme Q10, whilst most of the dextrose fraction is kept in separate units, capsules, tablets or the like. It is possible to add further substances such as fruit juice extracts, curcuma, tannin, a powder of Panax notoginseng, and Vinca rosea in suitable amounts. Oolong tea, aloe vera and spiral water algae might also be added. The composition or dietary supplementation may also be in the form of a liquid, in particular a sirup-type liquid. It is possible to provide the food composition in the appearance of a soft drink in a small bottle.

Preferably a dosage for a person with a body weight of about 80 kg includes a dextrose fraction of approx. 75%. Such a dosage is to provide a considerable moderation in degrading about 18 ml alcohol.

The composition is preferably constituted in a manner wherein a dosage of same, includes a dextrose fraction of about 75.2 mass %, i.e. a quantity of dextrose in the range from 7.2 to 12.8 g, preferably 10.0 g within a dose of 13.3 g.

The composition is preferably constituted in a manner wherein a dosage of same includes a Vitamin C fraction of about 7.5 mass % i.e. a quantity of Vitamin C in the range from 0.78 to 1.18 g, preferably 1.0 g, within a dose of 13.3 g.

The composition is preferably constituted in a manner wherein a dosage of same includes a L-glutamine and/or L-glutamic acid fraction of about 11.27 mass %, i.e. a quantity of said L-glutamine and/or L-glutamic acid fraction in the range from 1.23 to 1.7 g, preferably 1.5 g, within a dose of 13.3 g.

The composition is preferably constituted in a manner wherein a dosage of same includes a cysteine fraction of about 3.76 mass %, i.e. a quantity of said cysteine fraction in the range from 460 to 540 mg, preferably 500 mg, within a dose of 13.3 g.

The composition is preferably constituted in a manner wherein a dosage of same includes a riboflavin fraction of about 0.30 mass % i.e. a quantity of said riboflavin in the range from 32 to 48 mg, preferably 40 mg, within a dose of 13.3 g.

The composition is preferably constituted in a manner wherein a dosage of same includes a succinic acid fraction of about 0.752 mass %, i.e. a quantity of said succinic acid in the range from 90 to 110 mg, preferably 100 mg, within a dose of 133 g.

The composition is preferably constituted in a manner wherein a dosage of same includes a fumaric acid fraction of about 0.752 mass %, i.e. a quantity of said fumaric acid in the range from 90 to 110 mg, preferably 100 mg, within a dose of 13.3 g.

The composition is preferably constituted in a manner wherein a dosage of same includes a coenzyme Q10 fraction of about 0.451 mass %, i.e. a quantity of said coenzyme fraction in the range from 50 to 70 mg, preferably 60 mg, within a dose of 13.3 g.

The composition is preferably constituted in a manner wherein a dosage of same includes a niacin fraction of about 1 to 20 mg, preferably 15 mg within a dose of 13.3 g.

More preferably each ingredient of the composition other than niacin is in the range from about 0.01 to about 100 gram, preferably from about 0.05-50 gram, wherein niacin is in the range from about 1 to 20 mg.

The composition is considered to provide the following achievements:
1. Reduction of ethanol metabolism by slowing down the process of ethanol oxidation into acetaldehyde, to prevent accumulation of acetaldehyde in the first place.
2. Stimulation of the activity of ALDH and avoiding any blockade of its enzymatic activity.
3. Speeding up the reaction from acetaldehyde to acetic acid and the further decomposition in the citrate cycle.
4. Improving the levels of those anti-oxidants of the alcohol consumer, which specially protect against toxic effects of acetaldehyde.

The first achievement is believed to be reached by the intake of a large dose of dextrose sugar (glucose).

Glucose is rapidly oxidised in the cytosol of liver cells using, the same cytosol NAD pool used by ethanol to be converted into acetaldehyde. Because the amount of cytosolic NAD is limited and can only constantly be reproduced from NADH+H$^+$ much less acetaldehyde accumulates.

The second achievement is also believed to be achieved by the intake of a large dose of glucose. Glucose augments the enzymatic activity of ADH as well as of ALDH. When a large glucose load occurs in the cytosol of liver cells then there is no possibility that the acetaldehyde reaches levels which could lead to inactivation of ALDH or to mitochondrial destruction.

The third achievement is believed to be performed by a) Accelerating the reoxidation from NADH+H$^+$ to NAD by speeding up the transport of electrons through the inner mitochondrial membrane
b) Accelerating the Krebs cycle It is believed to be achieved by the inclusion of coenzyme $Q_{10}$ and riboflavin.

Riboflavin will quickly be transformed to FMN, which together with coenzyme $Q_{10}$ is the determining substance for the speed of the reoxidation of NADH+H$_+$ to NAD$_+$ in the mitochondrial matrix. Acetaldehyde needs NAD+ when it is metabolised to acetic acid. Within this reaction NAD is transformed into NADH+H$^+$. Because the availability of NAD is limited in the mitochondrial matrix NADH+H$^+$ has to be re-transformed into NAD to serve again for acetaldehyde decomposition. This reaction is only possible because FMN and coenzyme $Q_{10}$ absorb the electrons of NADH+H$^+$ and shuttle them through the mitochondrial membrane. The more FMN and coenzyme $Q_{10}$ are available, the more this process is speeded up and, because more NAD is available, the metabolism of acetaldehyde is accelerated.

It is known that the inclusion of coenzyme $Q_{10}$ decreases in the human body with progressing age.

The activation of the Krebs (citrate) cycle is achieved by the inclusion of succinic acid and fumaric acid. Both substances activate the second half of the citrate cycle and thereby activate the aerobic oxidation process in mitochondria. L-glutamic acid is quickly covert to L-glutamine after absorption in human body, and L-glutamine helps to speed up the mitochondria-cytosolic malate/asparate shuttle, which plays a key role in the course of intoxication by acetaldehyde. It also speeds up the succinate oxidation process by preventing oxalic and acetic inhibition of succinate dehydrogenase.

The fourth achievement, the elevation of anti-oxidant levels, is achieved by the inclusion of cysteine, ascorbic acid and also of L-glutamine and/or L-glutamic acid. Cysteine should provide a strong anti-oxidant effect as well as ascorbic acid. The human body transforms cysteine to gluthatione which specially protects against the toxic effects of acetaldehyde. To reach an optimal level of gluthatione and to avoid cysteine being transformed to cystine, it is important to combine cysteine with glutamine and give twice as much ascorbic acid as cysteine.

By administering the mentioned substances, the level of acetaldehyde after drinking alcohol will be remarkably reduced and flushing symptoms at least diminished. The other known side-effects of acetaldehyde such as headaches and hangovers should also disappear.

Thus, the present invention relates to a composition for reducing alcohol induced risk of neuropathy, neurodegenerative diseases including late-onset Alzheimer's disease and of cancer, in particular of esophageal, oropharyngolarynal, colorectal, lung, liver, breast and/or pancreatic cancer by moderating an alcohol degradation process in respect to ethanol metabolism within the human body. The composition of the present invention includes the following substances in physiologically relevant amount: niacin (Vitamin B3), dextrose, Vitamin C, L-glutamine and/or L-glutamic acid, cysteine, riboflavin, succinic acid, fumaric acid, and coenzyme Q10.

Furthermore, the compositions according to the present invention can be used as a pharmaceutical. The pharmaceutical or medicament, respectively, can be used for example for the manufacture of a medicament for the treatment and/or prophylaxis of cancer. By way of non-limiting example, such cancers can be selected from breast cancer, liver cancer, pancreatic cancer, esophageal cancer, colorectal cancer, lung cancer and oropharyngolaryngeal cancer.

In a further embodiment the composition of the present invention can also be used for the manufacture of a medicament for the prevention of tumour metastasis in general.

In a further embodiment, the composition of the present invention can also be used for the manufacture of a medicament for the treatment and/or prophylaxis of neuropathy and treatment and/or prophylaxis of a neurodegenerative disease, in particular of late-onset Alzheimer's Disease.

In a further embodiment the composition according to the present invention can also be used for the manufacture of a medicament for the treatment and/or prophylaxis of hangover, flushing syndrome, headache and/or alcoholic intoxication.

In a further embodiment the composition according to the present invention is present in the form of tablets. In a further embodiment a dose of the composition according to the present invention includes a plurality of small tablets or capsules. In particular said tablets or capsules can be contained in a dosage receptacle. In another embodiment the composition according to the present invention is of a sugar-cube type form. In another embodiment the composition according to the present invention is in the form of cryopowder. In another embodiment the composition according to the present invention is in the form of a small drink unit. In another embodiment the composition according to the present invention is in the form of a sirup.

In a further aspect the present invention relates to a composition, food or dietary supplementation, and pharmaceutical composition for reducing alcohol induced risk of neuropathy and/or neurodegenerative diseases including late-onset Alzheimer's disease, esophageal cancer, oropharyngolarynal cancer, breast cancer, liver cancer, lung cancer, colorectal cancer and/or pancreatic cancer, said composition including niacin for affecting an alcohol degrading process in particular in respect to ethanol metabolism within the human body, and substances, in particular substances mentioned above, providing the following effects within the human body: —Reducing ethanol metabolism by slowing down the process of ethanol oxidation into acetaldehyde, to prevent accumulation of acetaldehyde in the first place; —Stimulating the activity of ALDH and avoiding any blockade of its enzymatic activity; —Speeding up the reaction from acetaldehyde to acetic acid and further decomposition in the citrate cycle; —Improving the levels of those anti-oxidants of the alcohol consumer which specially protect against toxic effects of acetaldehyde.

As mentioned above, the present invention relates to a composition comprising niacin (Vitamin B3), dextrose, Vitamin C, L-glutamine and/or L-glutamic acid, cysteine, riboflavin, succinic acid, fumaric acid and coenzyme Q10. As mentioned above there are various embodiments of this composition.

EXAMPLES

Example 1

Supplement Solution and Animals

Ingredients of Supplement except Coenzyme Q10 were purchased from Sigma Aldrich Japan (Tokyo, Japan). Ten gram of dextrose, 1.0 gram of Vitamin C, 1.5 gram of L-glutamine, 500 mg of cysteine, 40 mg of riboflavin, 100 mg of succinic acid, 100 mg of fumaric acid, and 10 mg of niacin were dissolved in 100 ml of distilled water (Supplement Solution). One hundred mg of Coenzyme Q10 (Jarrow Formulas, Los Angels, Calif., USA) was dissolved in 14 ml of sesame oil.

Male, 6-week-old nude mice of BALB/cA-jcl-nu/nu class were purchased (Clea Japan Inc., Shizuoka, Japan) and allowed to acclimate for one week prior to the study. During the experiment the mice were maintained at a temperature of 23° C., 50% humidity and a specific-pathogen-free (SPF) condition.

Example 2

Cell Line and Metastatic Experiments

RPMI4788 cells derived from human colorectal cancer generate pulmonary metastasis in nude mouse (Moore G E & Koike A (1964), Cancer January, 17: 11-20; Kondo H. et al. (1987), Jpn J Cancer Res (Gann) 78, 12: 1400-1408). The cell line was subcultured in tissue culture flasks with culture medium of RPMI1640 solution (Nikken Biomedical Laboratory, Kyoto, Japan) supplemented with 10% Fetal Bovine Serum (FBS) (Hyclone Laboratories Inc., Logan, Utah) at 37° C., in an atmosphere of 100% humidity, 5% CO, and 95% air. Following isolation of the cultured cells by 0.02% EDTA, a cell suspension vas prepared using PBS of 0.01M; trypan blue staining confirmed cell viability over 98%.

To produce lung metastases, nude mice were injected cell suspension of $5 \times 10^4/0.1$ ml into tail vein. Twenty-eight days after the injection, all metastatic nodules on the lung surface were counted. The lung was fixed in 10% neutral formaldehyde and embedded in paraffin. Sections were stained with Hematoxylin-Eosin and examined histologically.

For testing the supplement, 320 μl of supplement solution and 50 μl of Co-Q10 dissolved sesame oil per mouse were administrated to the stomach by oral metal tube. For assaying the effects of Supplement+EtOH, one hour after the supplement administration, 7.0 ml/kg of ethanol were injected into the peritoneal cavity. Then 1 hour after the ethanol injection, $5 \times 10^4/100$ μl of RPMI4788 cells were injected into the tail vein. The nude mice were sacrificed 28 days after the cell injection and the metastatic nodules on the lung surface were counted.

The results of these experiments are shown below in table 1.

TABLE 1

| | Number of Metastatic nodules on the lung surface | | | |
|---|---|---|---|---|
| Exp. | 4788 (Control) | ETOH + 4788 | SUP + 4788 | SUP + ETOH ++ 4788 |
| | 14 | 48 | 28 | 49 |
| | 27 | 70 | 24 | 46 |
| | 31 | 64 | 54 | 80 |
| | 61 | 68 | 28 | 66 |
| | 41 | 75 | 40 | 46 |
| | 82 | 58 | 34 | 21 |
| | 37 | 69 | 45 | 64 |
| | 9 | 62 | 67 | 79 |
| | 16 | 18 | 21 | 9 |
| | 14 | 19 | 13 | 11 |
| | 14 | 21 | 15 | 12 |
| | 12 | 24 | 13 | 14 |
| | 16 | 19 | 11 | 16 |
| | 16 | 20 | 17 | 14 |
| | 17 | 21 | 16 | 15 |
| | 18 | 20 | 17 | 14 |
| Total | 425 | 676 | 443 | 556 |
| Average | 26.6 | 42.25 | 27.7 | 34.75 |

TABLE 1-continued

| | Number of Metastatic nodules on the lung surface | | | |
|---|---|---|---|---|
| Exp. | 4788 (Control) | ETOH + 4788 | SUP + 4788 | SUP + ETOH ++ 4788 |
| minus 4788 | 0 | 251 | 18 | 131 52.20% |

Two independent experiments with eight mice each were performed. Average metastatic nodules on lung surface in the Control (only 4788 cells): 26.6, Ethanol+4788 cells: 42.25, Supplement+4788 cells: 27.7, Supplement+Ethanol+4788 cells: 34.75. These results show that the supplement according to the invention did not effect the metastatic potential of 4788 cell line. Ethanol enhanced approximately 60% of metastatic potential of 4788 cell line. Supplement reduced half of metastasis which enhanced by ethanol. Difference between the group of Ethanol+4788 cells and Supplement+Ethanol+4788 cells are significantly ($P=0.03$) by t-test.

Example 3

NK-Activity

A short-term $^{51}$Cr-release assay was used to determine the natural killer (NK) cytotoxic activity. Mice were divided in following 3 groups; control, ethanol administration, and Supplement and ethanol administration. Twenty four hours after the ethanol administration, splenocytes of the nude mouse were separated as single cell suspension. Target YAC-1 cells ($1\times10^7$) were labeled by incubation with 200 µCi of $^{51}$Cr for 2 hours at 37° C. After being washed and then incubated for 2 hours at 37° C., the cells were supplemented in RPMI1640 medium 20 µl of the labeled target cells and 100 µl of effector cells were mixed into a 96-well microtiter plate (Sumitomo Bakelite Co., Ltd., Tokyo, Japan) at various effector/target cell ratios. After 4 hours of incubation, the plates were centrifuged and the radioactivity of the supernatant was measured by a gamma-counter. The percent of cytotoxicity was calculated as (experimental group release—spontaneous release/total release—spontaneous release). Statistical analysis of the results was conducted by $t^2$ test, and $p<0.5$ was defined as the level of significance. The results of this experiments are shown in the table 2 below.

TABLE 2

| | Spontaneous $^{51}$Cr release | Total $^{51}$Cr release | Control | EtOH | Supple. + EtOH |
|---|---|---|---|---|---|
| Average cont | 264.3 | 2966.3 | 930.6 | 568.6 | 771.8 |
| NK activity | | | 24.60% | 11.20% | 18.70% |
| % Control | | | | 45.5% | |
| % increase NK | | | | | 55.9 |

Thus, Ethanol reduced NK activity of control nude mice to 45.5%, and this effect induced by acetaldehyde as previously reported in many manuscripts. Supplement increased 55.9% NK activity which reduced by Ethanol. Supplement may reduce the acetaldehyde in nude mice like human and NK activity.

Example 4

Supplement Preparation, Human Volunteers and Alcohol

Ingredients of Supplement except Coenzyme Q10 were purchased from Sigma Aldrich Japan (Tokyo, Japan). AQUAQ10P40 (Nissin Pharma. Tokyo Japan) which is powder form and contains 40% of Coenzyme Q10 was used as Coenzyme Q10. One gram of Vitamin C, 1.5 gram of L-glutamic acid, 500 mg of cysteine, 40 mg of riboflavin, 100 mg of succinic acid, 100 mg of fumaric acid, 10 mg of niacin and 250 mg of AQUAQ10P40 (exact volume as 100 mg of Coenzyme Q10) were mixed. Supplement mixture was dissolved 100 ml water just before drink.

Four healthy adults volunteers (two mail and two female, age 26-48) were agreed with alcohol consumption and blood sampling. Four hundred ml of red wine which contains 12.5% of ethanol was used as alcohol, and this amount is exactly same as 50 gram of ethanol. Red wine was administered during the first interval of 30 minute from the start of experiments. Control and supplement study was examined different date.

Example 5

Blood Sampling, and the Measurement of Blood Ethanol and Acetaldehyde

Blood sample was taken at the following 4 times: before the alcohol administration (0), and 30, 60, and 90 minutes after alcohol administration (30, 60, 90 min). Supplement was orally taken with 100 ml water 20 minutes before the administration. For the ethanol measurement, whole blood was stored at 4° C. in heparin coated tube. For the acetaldehyde measurement, blood samples were immediately centrifuged by heparin coated tube at 1500 rpm×10 minutes, and serum were frozen at −80° C. Ethanol and acetaldehyde were measured by bio medical laboratories company BML, INC. (Shibyya-ku, Tokyo, Japan). Statistical analysis of the results was conducted by $t^2$ test, and $p<0.5$ was defined as the level of significance. The results of this blood ethanol experiments are shown in the table 3 below.

TABLE 3

| The effects of supplement on human blood ethanol | | | | |
|---|---|---|---|---|
| | Time | | | |
| | 0 | 30 min | 60 min | 90 min |
| without SUP | 0 | 83.75 | 80.75 | 70.25 |
| with SUP | 0 | 24.75 | 50.75 | 45 |

(Data indicated are average of 4 sample. mg/dl)

The supplement (composition of the present invention) reduced the blood ethanol level in comparison to the control at the time points 30, 60 and 90 minutes after administration of the alcohol. Significant difference ($P<0.05$) was observed between control and supplement study at the time 60 and 90 minutes.

The results of this blood acetaldehyde experiments are shown in the table 4 below.

TABLE 4

The effects of supplement on human blood acetaldehyde

| | Time | | | |
|---|---|---|---|---|
| | 0 | 30 min | 60 min | 90 min |
| without SUP | 0 | 2.125 | 1.65 | 1.7 |
| with SUP | 0 | 0.575 | 0.475 | 0.475 |

(Data indicated are average of 4 sample. μM)

The supplement (composition of the present invention) keeps low blood acetaldehyde level in comparison to the control at the time points 30, 60 and 90 minutes after administration of the alcohol. Significant difference (P<0.05) was observed between control and supplement study at the time 30, 60 and 90 minutes.

Example 6

Comparison of Composition of the Present Invention and Amino De Kanpai

Amino de Kanpai is a product of Ajinomoto (Tokyo, Japan) which is sold in Japanese market since March 2006, and contains 1.4 gram of Glutamine and 1.4 gram of Alanine. Ajinomoto markets Amino de Kanpai as an alcohol reducing compositions for human subjects. Furthermore, the compositions should reduce headache and discomfort caused by alcohol. In this experiments, all conditions of the experiment is identical to the conditions of Example 4 and 5 above except that 3 volunteers participated and one portion of Amino de Kanpai (3.0 gram) was administered 20 minutes before the administration of alcohol. The results of blood ethanol levels with Amino de Kanpai, and correspondent data of control and supplements (SUP: composition of the present invention) are shown in the table 5 below.

TABLE 5

Comparison of composition of the present invention and Amino de Kanpai

| | Time | | | |
|---|---|---|---|---|
| | 0 | 30 min | 60 min | 90 min |
| Control | 0 | 57.6 | 79 | 70 |
| with Amino de Kanpai | 0 | 58.3 | 71 | 61 |
| with SUP | 0 | 26 | 54.3 | 48.3 |

(Data indicated are average of 3 sample. mg/dl)

Amino de Kanpai showed slight effects of ethanol reduction compare to the control. Reduction ratio of ethanol at the 90 minutes was 12.8% for Amino de Kanpai, and 31% for SUP. There was no significant difference between Amino de Kanpai and control by $t^2$ test.

The invention claimed is:

1. A method of treating a disease or condition selected from the group consisting of alcohol-induced lung cancer, alcohol-induced neuropathy, alcohol-induced late-onset Alzheimer's disease, hangover syndrome, flushing syndrome, alcohol-induced headache and/or alcoholic intoxication comprising administering to a subject suffering one of the foregoing diseases or conditions a dose of a composition comprising:

Niacin at 1 to 20 mg, dextrose at 7.2 to 12.8 g, Vitamin C at 0.78 to 1.18 g, L-glutamine at 1.23 to 1.7 g and/or L-glutamic acid at 1.23 to 1.7 g, cysteine at 460 to 540 mg, riboflavin at 32 to 48 mg, succinic acid at 90-110 mg, fumaric acid at 90 to 110 mg and coenzyme Q10 at 50-70 mg.

2. The method according to claim 1, wherein the disease is alcohol-induced late-onset Alzheimer's Disease.

3. The method according to claim 1, wherein the disease is alcohol-induced lung cancer.

4. The method according to claim 1, wherein the disease is alcohol-induced neuropathy.

* * * * *

UNITED STATES PATENT AND TRADEMARK OFFICE
CERTIFICATE OF CORRECTION

| | | |
|---|---|---|
| PATENT NO. | : 8,580,750 B2 | Page 1 of 1 |
| APPLICATION NO. | : 11/997127 | |
| DATED | : November 12, 2013 | |
| INVENTOR(S) | : Mattuschka-Greiffenclau | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1261 days.

Signed and Sealed this
Tenth Day of March, 2015

Michelle K. Lee
*Deputy Director of the United States Patent and Trademark Office*